United States Patent
Yoshida et al.

(10) Patent No.: US 11,723,573 B2
(45) Date of Patent: Aug. 15, 2023

(54) STRETCHABLE RAISED ELECTRODE AND METHOD OF MANUFACTURING THEREOF

(71) Applicant: National Institute of Advanced Industrial Science and Technology, Tokyo (JP)

(72) Inventors: Manabu Yoshida, Ibaraki (JP); Taiki Nobeshima, Ibaraki (JP); Kazunori Kuribara, Ibaraki (JP); Takeshi Kobayashi, Ibaraki (JP); Toshihiro Takeshita, Ibaraki (JP)

(73) Assignee: National Institute of Advanced Industrial Science and Technology, Tokyo (JP)

(*) Notice: Subject to any disclaimer, the term of this patent is extended or adjusted under 35 U.S.C. 154(b) by 786 days.

(21) Appl. No.: 16/480,350

(22) PCT Filed: Jan. 24, 2018

(86) PCT No.: PCT/JP2018/002107
§ 371 (c)(1),
(2) Date: Jul. 24, 2019

(87) PCT Pub. No.: WO2018/139483
PCT Pub. Date: Aug. 2, 2018

(65) Prior Publication Data
US 2019/0380606 A1    Dec. 19, 2019

(30) Foreign Application Priority Data
Jan. 25, 2017   (JP) ................. 2017-011461

(51) Int. Cl.
*A61B 5/25*    (2021.01)
*A61B 5/00*    (2006.01)
(Continued)

(52) U.S. Cl.
CPC ............... *A61B 5/25* (2021.01); *A61B 5/291* (2021.01); *A61B 5/6803* (2013.01); *H01M 50/533* (2021.01)

(58) Field of Classification Search
CPC ......... A61B 5/25; A61B 5/291; A61B 5/6803; A61B 5/6804; A61B 5/256; H01M 50/538; B05C 19/002
See application file for complete search history.

(56) References Cited

U.S. PATENT DOCUMENTS

| | | | |
|---|---|---|---|
| 2014/0135608 A1* | 5/2014 | Gazzoni | A61B 5/24 427/2.12 |
| 2016/0133352 A1* | 5/2016 | Hashimoto | C08J 7/0427 428/297.4 |
| 2018/0263518 A1* | 9/2018 | Shimuta | A61B 5/02108 |

FOREIGN PATENT DOCUMENTS

| JP | H05137699 A | 6/1993 |
|---|---|---|
| JP | 2011036524 A | 2/2011 |

(Continued)

OTHER PUBLICATIONS

Wu, H.P., et al., "High conductivity of isotropic conductive adhesives filled with silver nanowires", Nov. 28, 2005, INternational Journal of Adhesion and Adhesives, pp. 615-621 (Year: 2005).*
(Continued)

*Primary Examiner* — Adam Z Minchella
(74) *Attorney, Agent, or Firm* — McCormick, Paulding & Huber PLLC (57) ABSTRACT

A stretchable raised electrode having a stretch property that can be used as a biological electrode for collecting biological signals while being pressed against a body is provided, and a method of manufacturing the stretchable raised electrode is provided. This raised electrode is a raised electrode formed by raising a surface of a sheet material having the stretch property. This raised electrode includes: a resin layer configured to be stretchable to follow the surface of the sheet material; and a plurality of conductive fibers each having an inserted portion, one end of which is inserted into the resin layer. The conductive fibers that are adjacent to one another
(Continued)

are electrically in contact with one another at non-inserted portions into the resin layer, and the conductive fibers are formed in the resin layer so as to have such a density as causing an in-plane isotropic electric conductivity of an electrode region of the sheet material in which the conductive fibers are formed. This raised electrode can be obtained by an electrostatic spraying method.

12 Claims, 8 Drawing Sheets

(51) Int. Cl.
  *A61B 5/291* (2021.01)
  *H01M 50/533* (2021.01)

(56) References Cited

FOREIGN PATENT DOCUMENTS

| | | |
|---|---|---|
| JP | 2012176120 A | 9/2012 |
| JP | 2015016166 A | 1/2015 |
| JP | 2015213607 A | 12/2015 |
| JP | 2016212986 A | 12/2016 |

OTHER PUBLICATIONS

Akter, Tahmina, et al., "Reversibly Stretchable Transparent Conductive Coatings of Spray Deposited Silver Nanowires", Apr. 3, 2012, ACS Publications, pp. 1855-1859 (Year: 2012).*

Kim Taegeon, et al., "Electrostatic Spray Deposition of Highly Transparent Silver Nanowire Electrode on Flexible Substrate", Dec. 31, 2012, ACS Publications, pp. 788-794 (Year: 2012).*

International Search Report For Serial No. PCT/JP2018/002107 dated Apr. 12, 2018.

Akter et al., "Reversibly Stretchable Transparent Conductive Coatings of Spray-Deposited Silver Nanowires", ACS Applied Materials & Interfaces, vol. 4, No. 4, Apr. 25, 2012, p. 1855-1859.

Kim et al., "Electrostatic Spray Deposition of Highly Transparent Silver Nanowire Electrode on Flexible Substrate", ACS Applied Materials & Interfaces, vol. 5, No. 3, Jan. 30, 2013, p. 788-794.

Extended European Search Report For European Patent Application No. 18 745 420.2 dated Jun. 23, 2020.

* cited by examiner

3D200/40 (GAUZE THICKNESS 155 μm)

(c)

STRETCHABLE RAISED ELECTRODE AND METHOD OF MANUFACTURING THEREOF

CROSS-REFERENCE TO RELATED APPLICATIONS

This application is a National Stage application of International Patent Application No. PCT/JP2018/002107, filed on Jan. 24, 2018, which claims priority to Japanese Patent Application No. 2017-011461, filed on Jan. 25, 2017, each of which is hereby incorporated by reference in its entirety.

TECHNICAL FIELD

The present invention relates to a raised electrode formed by raising a conductive fiber on a surface of a sheet material, and relates to a method of manufacturing thereof, and, particularly relates to a stretchable raised electrode that has a stretch property and that can be used as a biological electrode or others collecting biological signals while being pressed against a body, and relates to a method of manufacturing thereof.

BACKGROUND

A flexible electrode that has flexibility and that can cause electric current flow between the electrode and an uneven object while being pressed against a surface of the object. As one of such flexible electrodes, a biological electrode used as a measuring electrode collecting biological signals while being pressed against a body is cited. For example, a biological electrode made of a conductive sheet is pressed against a torso part of a human body through a conductive gel applied therebetween, and the biological signals of electrocardiogram or others are collected. The conductive gel described here is used to electrically fill between the torso part and the biological electrode so that weak electric current can be reliably measured.

Incidentally, in a case of sensitive skin, it is not preferable to bring the conductive gel directly in contact with the skin. Besides, also in a case of intended use of the gel over a long time such as application in a wearable electrode, it is required to avoid the usage of the conductive gel. Accordingly, it is proposed to, for example, use an electrode material having the elasticity or stretch property or implant/raise a conductive fiber on a surface of the electrode material so as to allow the weak electric current of the biological body to be collected while following along the surface of the uneven object even if the conductive gel is not used.

For example, Japanese Patent Application Laid-Open Publication No. 2011-36524 discloses a biological electrode in which a detection unit having the electric conductivity and flexibility such as a fabric made of the conductive fibers is arranged around a holding unit having the elasticity and thickness such as a sponge. Owing to deformation of this biological electrode placed inside a cloth, the adhesiveness onto the biological body can be enhanced, but the electrode does not have the stretch property. Meanwhile, Japanese Patent Application Laid-Open Publication No. H05-137699 discloses a biological electrode obtained by unifying the fabric member having the stretch property with a strip electrode made of the conductive fiber by continuous non-woven fabric process, weaving process, or braiding (knitting) process. In this biological electrode, although the fabric member serving as a base material stretches/shrinks, the strip electrode part does not stretch/shrink. Accordingly, it can be thought that, for example, a conductive stretchable film as disclosed in Japanese Patent Application Laid-Open Publication No. 2016-212986 is used for the strip electrode.

Japanese Patent Application Laid-Open Publication No. 2015-16166 discloses a raised electrode obtained by protruding and extending a plurality of contacts each made of a conductive fiber from a base in a raised state, as a biological electrode for collecting brain waves although this is not the electrode made of the sheet material. In this electrode, although the base does not stretch/shrink, the electrode substantially stretches/shrinks when the contacts flexibly move.

SUMMARY

In a biological electrode in which an electrode portion made of a metal film is arranged on a sheet material having the stretch property, the sheet material can stretch/shrink while the electrode portion does not stretch/shrink. Such a biological electrode limits action of a (electrode-)wearing person and causes a lack of comfortableness, and is not particularly preferable as a wearable electrode. Accordingly, a raised electrode provided with a raised portion made of the conductive fiber on the sheet material having the stretch property has been thought. However, when a current-collecting portion that collects an electric current from a lot of raised portions is formed along the surface of the sheet material, it is necessary to achieve electrical and mechanical connection with the conductive fibers, and necessary to follow the stretching/shrinkage of the sheet material, and therefore, it is not easy to achieve a structure for these purposes.

The present invention has been made in consideration of the circumstances as described above, and an object of the present invention is to provide a stretchable raised electrode that has a stretch property and that can be used as a biological electrode to collect biological signals while being pressed against a body, and is to provide a method of manufacturing the stretchable raised electrode.

A raised electrode according to the present invention is a raised electrode obtained by raising a surface of a sheet material having a stretch property, and the raised electrode has a feature including: a resin layer configured to be stretchable so as to follow along the surface of the sheet material; and a plurality of conductive fibers each having an inserted portion, one end of which is inserted into the resin layer, the adjacent conductive fibers are electrically in contact with one another at non-inserted portions into the resin layer, and the conductive fiber is formed in the resin layer so as to have such a density as causing an in-plane isotropic electric conductivity in an electrode region of the sheet material having the conductive fiber.

The invention can provide the conductive property that is enough for the electrode even if the resin layer does not have the high electric conductivity, and therefore, an optional range for the material of the resin layer supporting the sheet material can be widened, so that it can be easy to form the conductive fiber, and besides, an optional range for a mode of this formation can be widened.

The above-described invention may have a feature in which the conductive fibers that are adjacent to one another and that have a contact point among them incline from the sheet material so as to maintain the contact point by the stretch/shrinkage of the sheet material. According to the invention, a stable electric conductivity can be obtained.

The above-described invention may have a feature in which the conductive fiber has a smaller length of the inserted portion than that of the non-inserted portion. And, the above-described invention may have a feature in which the length of the non-inserted portion of the conductive fiber is twice or more as long as the length of the inserted portion. Further, the above-described invention may have a feature in which the length of the conductive fiber is 1 mm or shorter. According to the invention, the conductive fiber can stably function as the electrode without being affected by the stretch/shrinkage of the sheet material.

The above-described invention may have a feature in which the conductive fiber is a needle-shaped body having an electric-conductive plated surface of the fiber. According to the invention, the conductive fiber can stably function as the electrode without being affected by the stretch/shrinkage of the sheet material.

The above-described invention may have a feature in which the resin layer is an insulator. According to the invention, an optional range for the material of the resin layer supporting the sheet material can be widened, so that the conductive fiber can be easily formed, and besides, an optional range for the formation mode can be widened.

A method of manufacturing a raised electrode according to the present invention is a method of manufacturing a raised electrode formed by raising a surface of the sheet material having a stretch property, the raised electrode including: a resin layer configured to be stretchable so as to follow along the surface of the sheet material; and a plurality of conductive fibers each having an inserted portion, one end of which is inserted into the resin layer, and the method has a feature including: a step of forming an adhesive layer on the surface of the sheet material; a raising step of raising the surface by making the conductive fibers fly toward the surface so that one end is inserted into the adhesive layer; and a hardening step of hardening the adhesive layer to form the resin layer, the conductive fibers that are adjacent to one another are electrically in contact with one another at non-inserted portions into the resin layer, and the conductive fibers are formed so as to have such a density as causing an in-plane isotropic electric conductivity in an electrode region of the sheet material in which the conductive fibers are formed.

The invention can provide the conductive property that is enough for the electrode even if the resin layer does not have the high electric conductivity, and therefore, an optional range for the material of the resin layer supporting the sheet material can be widened, so that it can be easy to form the conductive fiber, and besides, an optional range for a mode of this formation can be widened.

The above-described invention may have a feature in which the raising step includes a spraying step of spraying the charged conductive fiber from an electrostatic spray gun toward the sheet material with a voltage applied between the electrostatic gun and an earthed electrode on which the sheet material is placed. According to the invention, the conductive fiber can be effectively fuzzed.

The above-described invention may have a feature in which the voltage is adjusted in the spraying step so that the length of the inserted portion of the conductive fiber is smaller than that of the non-inserted portion thereof. And, the above-described invention may have a feature in which the length of the non-inserted portion of the conductive fiber is twice or more as long as the length of the inserted portion thereof in the spraying step. According to the invention, a stable electrode can be obtained without being affected by the stretch/shrinkage of the sheet material.

DETAILED DESCRIPTION

As one example according to the present invention, a raised electrode will be described in detail with reference to FIG. 1.

Figure 1:
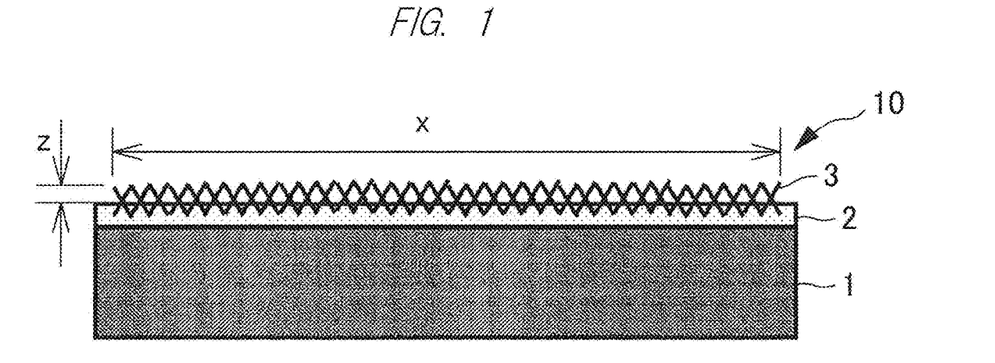
FIG. 1 is a cross-sectional view of a raised electrode in one example of the present invention.

As shown in FIG. 1, a raised electrode 10 includes: a base member 1 made of a sheet material having a stretch property; a resin layer 2 bonded on a surface of the base member; and a plurality of conductive fibers 3, one end of each of which is implanted to be inserted into the resin layer 2. In this case, the conductive fibers 3 are formed so that the adjacent fibers are electrically in contact with one another at non-inserted portions that are not inserted into the resin layer 2, and are configured so as to have such a density as causing a state in which an electric conductivity of an electrode region formed in the raised electrode 10 is isotropic in a plane. In this case, the electrode region is a region from which the non-inserted portions of the conductive fibers 3 are exposed toward a main surface side of the raised electrode 10, such as a region in a range indicated by "x" in a lateral direction and "z" in a height direction in the drawing. Even in a top view, the region is similarly a region from which the conductive fibers 3 are exposed.

The base member 1 is not particularly limited as long as it is the sheet material having the stretch property. For example, a fabric made of a synthetic fiber such as nylon and polyester, a sheet made of thermosetting resin-based elastomer such as urethane, a sheet made of synthetic rubber such as butyl rubber, a sheet made of synthetic polymer compound such as silicon, or others can be used. According to a method of spraying the conductive fibers 3 by using an electrostatic spray method as described later, the base member 1 can have an insulating property.

The resin layer 2 is a layer made of an adhesive that can cause the formation mode of the conductive fibers 3 on the surface of the base member 1 as described above. For example, a silylated urethane-based elastic adhesive, an emulsion-based adhesive such as acrylic emulsion, or others can be used. Note that the resin layer 2 does not particularly need the conductive property, and therefore, a favorable material for obtaining the electrode region based on the conductive fibers 3 as described above such as a material having high adhesiveness on the base member 1 or others can be selected regardless of the conductive property. For example, selection of the material from the insulating material is preferable for the base member 1 and the resin layer 2 because the optional range for the material can be wider than that of the conductive material.

For the conductive fiber 3, for example, carbon nanofiber, metallic fiber, chemical fiber coated with conductive polymer or plated with metal, or others can be used. A fiber diameter of and a fiber length of the conductive fiber 3 are appropriately selected so as to cause the formation mode as described above. In consideration of the electric conductivity of the electrode region, the following ability for the deformation of the raised electrode 10, the flexibility and comfortableness of the electrode caused when the electrode is in contact with the body as the biological electrode, and others, the conductive fiber 3 is preferably, for example, a short fiber having a needle-shaped body with a fiber diameter that is equal to or smaller than 20 μm and a fiber length that is equal to or larger than 0.1 mm and equal to or smaller than 0.5 mm. In order to obtain the formation mode of the conductive fibers 3 as described above and make the conductive fibers 3 function as the electrode that is suitable for the stretch/shrinkage and the deformation required for the raised electrode 10, the number of the conductive fibers 3 per unit area and the inclination from the base member 1 (an angle made from the main surface of the base member 1) are set in accordance with the fiber diameter and the fiber length.

[Manufacturing Method]

Next, as one example according to the present invention, a method of manufacturing the raised electrode 10 by using the spraying step for the raising step will be described with reference to FIG. 2.

Figure 2:
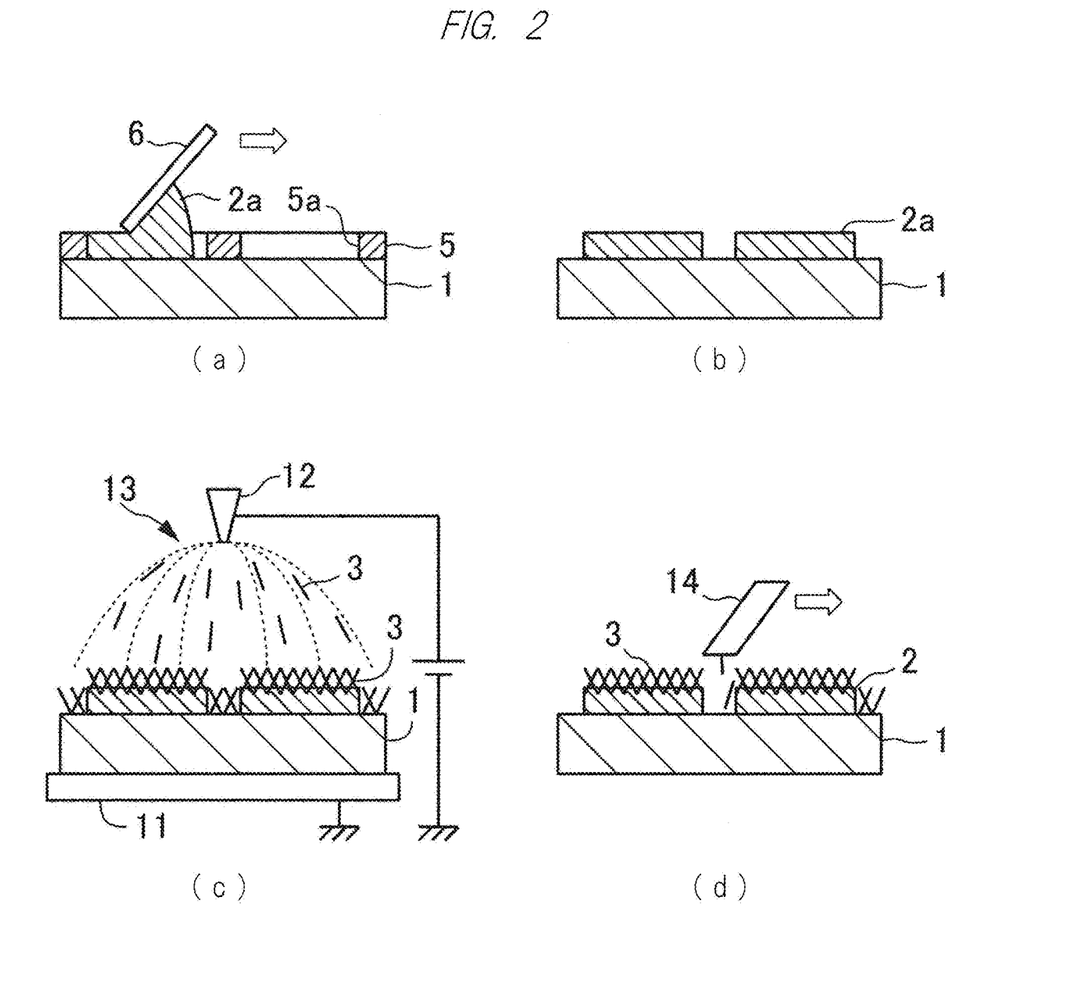
FIG. 2 is a process drawing showing a method of manufacturing the raised electrode.

As shown in FIG. 2(*a*), first, the adhesive 2*a* for forming the resin layer (adhesive layer) 2 is applied on the base member 1, and the electrode region is patterned. For example, a mask 5 having an opening 5*a* to be an electrode pattern is placed, and the adhesive 2*a* to be the resin layer 2 is spread on the mask by using a squeegee 6. In this case, the adhesive 2*a* is preferably configured to have such a viscosity as preventing occurrence of creases on the base member 1, for example, a viscosity of 10 to 400 Pa·s.

As shown in FIG. 2(*b*), after the mask 5 is removed, the electrode pattern made of the adhesive 2*a* can be formed. Note that a thickness of the mask 5, that is, a thickness of the resin layer 2 made of the adhesive 2*a* formed on the base member 1 allows the conductive fibers 3 to be implanted, and is preferably, for example, 10 to 1000 μm. For the patterning of the adhesive 2*a*, note that other methods such as a screen printing method, a stencil printing method, a dispensing method, a spray coating method and an inkjet method can be also used.

As shown in FIG. 2(*c*), the conductive fibers 3 are sprayed by using the electrostatic spraying method. That is, the charged conductive fibers 3 are sprayed from the electrostatic spray gun 12 onto the base member 1 in a state in which the voltage is applied between the electrostatic spray gun 12 and the earthed electrode 11 on which the base member 1 is placed. The conductive fibers 3 fly and are drawn a long line of electric force 13 to the electrode 11. As a result, the conductive fibers 3 are implanted into the adhesive 2*a* having the thickness so that one end of each conductive fiber is inserted therein to cause the raised fiber by an initial velocity caused by the spraying and an electrostatic force, or the conductive fibers 3 directly fall down on a part of the base member 1 except for the electrode pattern. A length of the inserted portion of the conductive fiber 3 into the adhesive 2*a* can be controlled by adjusting the voltage between the electrode 11 and the electrostatic spray gun 12. Other publicly-known methods such as a spray coating method and an electrostatic flocking (implanting) method may be used as long as the one end of the conductive fiber 3 can be inserted into the resin layer 2.

As shown in FIG. 2(*d*), in the hardening step, the adhesive 2*a* is made dry or others and hardened to become the resin layer 2, and the conductive fibers 3 that have flown and directly fallen down on the base member 1 are sucked and removed by using a vacuum cleaner 14. The conductive fibers may be removed by using a weak-adhesion roller or others. In this manner, the raised electrode 10 having the electrode region where the conductive fibers 3 are implanted onto the electrode pattern can be obtained.

Further, a portion that is not used as the electrode region may be a wiring region where an insulating film is formed on the conductive fibers 3. That is, the insulating film is formed by compressing and bonding an insulating sheet or applying an insulating paste and making the paste dry. For such an insulating film, an urethane elastomer, a silicon resin, a butyl rubber-based material that are excellent in the stretch property and the flexibility are suitable.

[Principle]

Next, when the raised electrode 10 is used as the biological electrode, a principle for maintaining the electric conductivity under the stretch/shrinkage and the following of the deformation will be described with reference to FIGS. 3 and 4.

Figure 3:
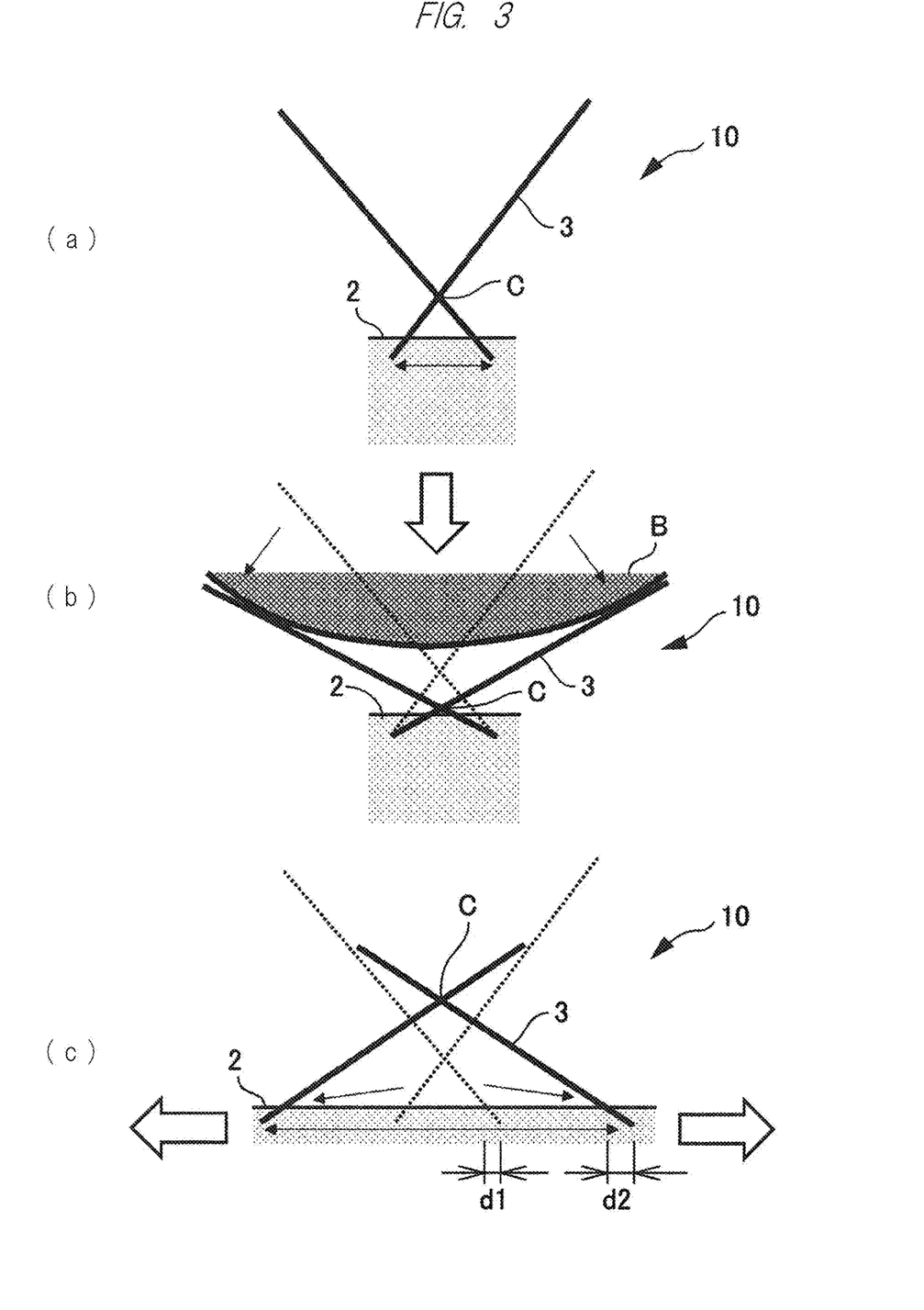
FIG. 3 is a diagram for explaining a principle of the raised electrode following deformation or others by using a conductive fiber.

As shown in FIG. 3(*a*), the conductive fibers 3, one end of each of which is inserted into the resin layer 2 in an initial state, are electrically connected to one another at a contact point "C" of each of the non-inserted portions.

As shown in FIG. 3(*b*), when an object "B" is pressed from above such a raised electrode 10, the conductive fibers 3 are inclined in a direction of decreasing the thickness of the raised electrode 10. That is, the inclinations of the conductive fibers 3 are increased in a direction of bringing the other ends of the conductive fibers 3 close to the resin layer 2, in other words, a direction of decreasing an angle from the main surface of the base member 1 (see FIG. 1) to lay the fibers down, so that the thickness of the electrode region decreases. Also in this case, the contact point C is maintained at a position at which the conductive fibers 3 are closer to the resin layer 2, and the electrical connection can be maintained. Note that a plurality of the conductive fibers 3 are practically three-dimensionally in contact with one another, and it is preferable to arrange some adjacent conductive fibers 3 with such a density as causing a plurality of contact points C in order to cause the in-plane isotropic electric characteristics. According to this, both the base member 1 and the resin layer 2 can have the insulation property.

As shown in FIG. 3(*c*), when the raised electrode 10 is stretched in a direction along the main surface of the base member 1 (see FIG. 1), the inserted portions of the conductive fibers 3 having the contact point C among them are away from one another. In this case, a distance "d2" in a stretch direction between the deepest part of and a surficial part of the inserted portion of the conductive fiber 3 is larger than a distance "d1" of the same before the stretch because of the stretch of the stretchable resin layer 2. By the deformation from the distance d1 to the distance d2, the conductive fiber 3 is inclined so that the angle of the conductive fiber 3 from the main surface of the base member 1 decreases. In this manner, the contact point C can be maintained to be closer to the tip end side (the other end side) of the conductive fiber 3. Although the density of the conductive fibers 3 in the electrode region tends to be reduced by the deformation in the stretch direction, the reduction in this density can be cancelled to some extent by such deformation as thinning the electrode region in the thickness direction, and therefore, it is easy to maintain the electric connection in the electrode region.

Note that the change of the angle of the conductive fiber 3 caused by the stretch of the resin layer 2 can be caused when the inserted portion of the conductive fiber 3 is sufficiently smaller than the non-inserted portion thereof, and a ratio in the length therebetween is representatively twice or more, that is, "inserted portion:non-inserted portion"=1:2, more preferably 1:3 to 5. When this ratio is too large, note that the conductive fiber 3 changes in a shape or easily falls out at the time of the pressing of the object B as shown in FIG. 3(b).

Based on the principle as described above, the raised electrode 10 having the stretch property can be used as the biological electrode collecting the biological signals while being pressed against the body. That is, the raised electrode 10 forms a three-dimensional network in which the conductive fibers 3 are electrically connected to one another, and can maintain the in-plane isotropic electric conductivity even when deforming because of following a curved surface or deforming in the thickness direction because of the pressing, and therefore, is suitable to be used as the biological electrode.

As described above, since the electric conductivity can be maintained by the electrode region made by the conductive fibers 3, the resin layer 2 does not need the electric conductivity as described above, and the optional range for the material of the resin layer 2 supporting the base member 1 can be widened so that the conductive fibers 3 can be implanted in the favorable formation mode.

Figure 4:
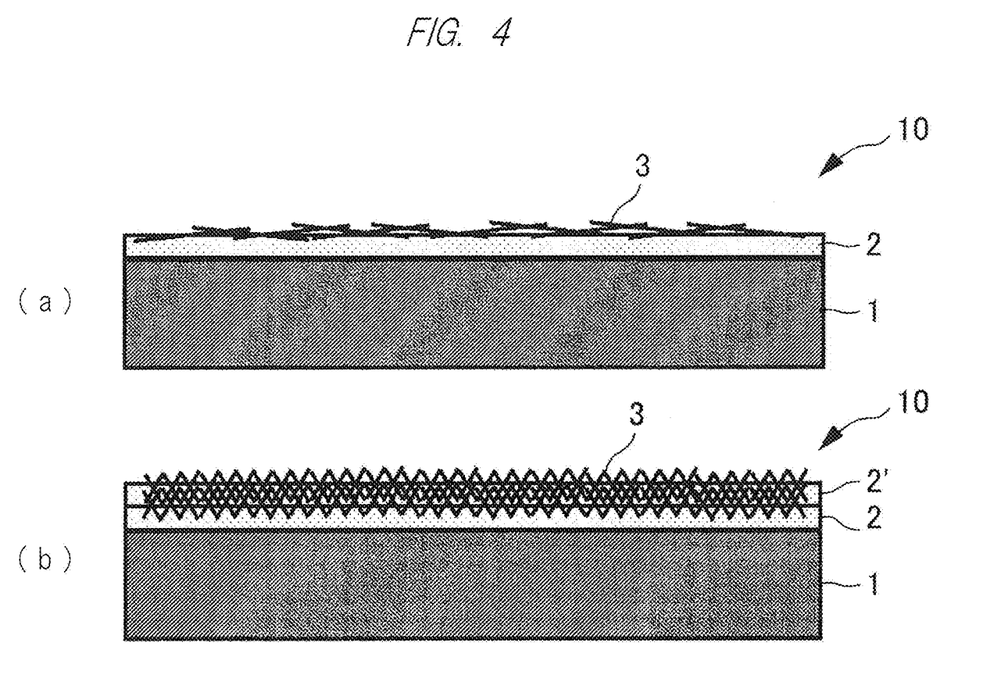
FIG. 4 is a cross-sectional view showing another example of the raised electrode.

As shown in FIG. 4(a), in the raised electrode 10, note that the angle of the conductive fiber 3 from the main surface of the base member 1 can be made small. The raised electrode 10 (see FIG. 1) having the large angle can easily follow the deformation caused by the pressing. On the other hand, by the small angle, the electric conductivity can be easily maintained against the stretch in the direction along the main surface of the base member 1.

As shown in FIG. 4(b), in the raised electrode 10, the electrode region made of the resin layer 2 and the conductive fibers 3 can be layered. In this case, the resin layer 2' overlaid on the conductive fibers 3 includes the electrode region having the electric conductivity even inside itself. By the layering of the resin layers 2 and 2', the deformation in the thickness direction can be easier to be followed, and besides, the electric connection can be maintained in the resin layer 2' so that the electric conductivity can be more stably maintained.

[Evaluation Test]

Next, results obtained by performing an evaluation test after the raised electrode 10 is manufactured will be described with reference to FIGS. 5 to 8.

Figure 5:
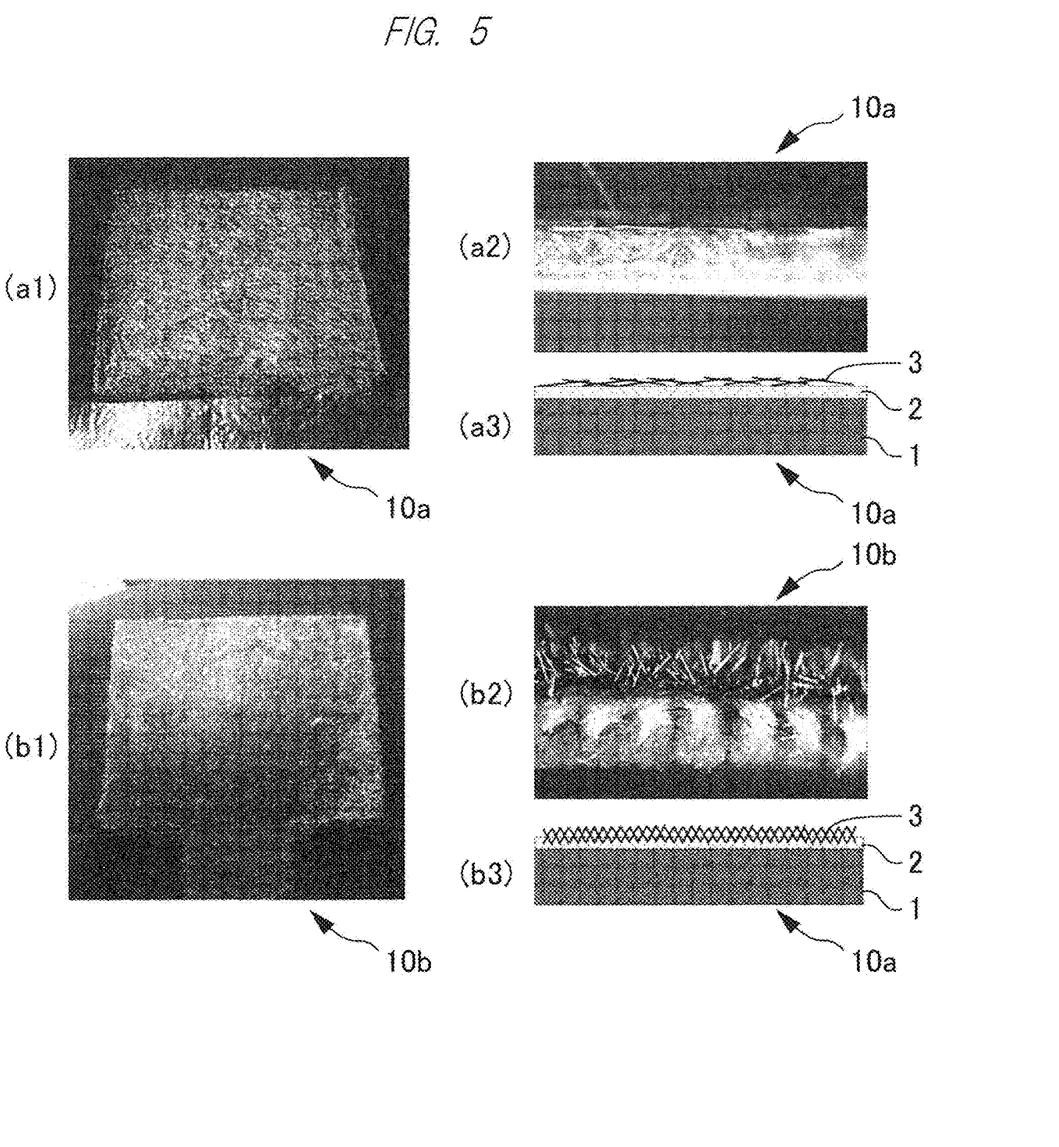
FIG. 5 is an exterior picture, a cross-sectional picture and a cross-sectional schematic view of a raised electrode used in an evaluation test.

As shown in FIGS. 5(a1) and 5(b1), two types of raised electrodes 10a and 10b were manufactured. That is, as shown in cross-sectional pictures and cross-sectional views of FIGS. 5(a2), (a3), (b2) and (b3), the raised electrode 10a having the small angle of the conductive fiber 3 from the main surface of the base member 1 and the raised electrode 10b having the large angle were manufactured. Note that a silver plated fiber having a fiber diameter of 17 μm and a length of 0.5 mm was used as the conductive fiber 3.

Figure 6:
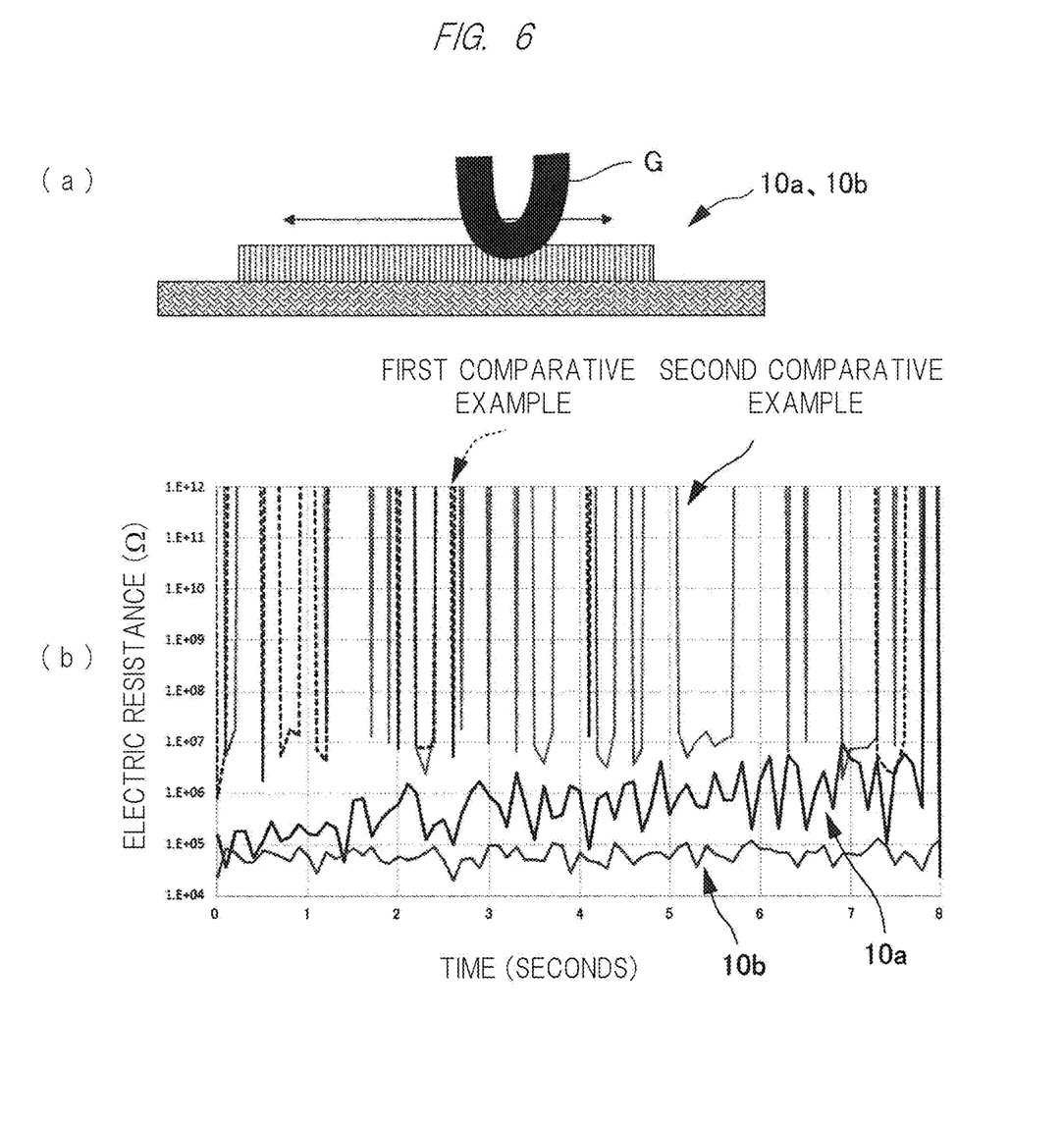
FIG. 6 is a diagram for explaining an evaluation test of sliding a conductive rubber on the raised electrode, and a graph of electric resistance change indicating results of the test.

As shown in FIG. 6(a), an electrical resistance between the raised electrodes 10a and 10b and a conductive rubber "G" caused when the conductive rubber G is slid on the raised electrodes 10a and 10b while being pressed against the raised electrodes was measured. An electrode formed by applying an Ag paste on the base member 1 and drying the paste was used for a first comparative example while a copper plate electrode was used for a second comparative example, and the electrical resistance caused when the conductive rubber G is slid on the electrodes while being pressed was similarly measured.

As shown in FIG. 6(b), the raised electrodes 10a and 10b are smaller in the electrical resistance and smaller in a degree of the change of the electrical resistance than those of the first and second comparative examples so as to have the consecutive in-plane isotropic change. It is thought that this is because the raised electrodes 10a and 10b deform while following the shape of the tip end of the pressed conductive rubber G and obtain a lot of contact points with the conductive rubber G to increase a contact area. And, it is thought that the deformation with good following ability is achieved even in the slide of the conductive rubber G because of the deformation of the conductive fibers 3, and thus, the number of contact points with the conductive rubber G can be maintained. Note that the raised electrode 10b having the large angle of the conductive fiber 3 from the main surface of the base member 1 is smaller in the electric resistance than the raised electrode 10a having the small angle thereof. It is considered that this is because the deformation caused by the pressing can be easier to be followed in the larger angle of the conductive fiber 3 as described above.

On the other hand, in the first comparative example (using the Ag-paste electrode) and the second comparative example (using the copper plate), the following ability for the shape change in the thickness direction is bad, and therefore, the contact area with the pressed conductive rubber G is adversely reduced. And, it is thought that it is difficult to follow the shape change caused by the movement of the conductive rubber G even if the electrode slides, and thus, the small contact area is further reduced or others, which results in inconsecutive large change of the electric resistance.

Figure 7:
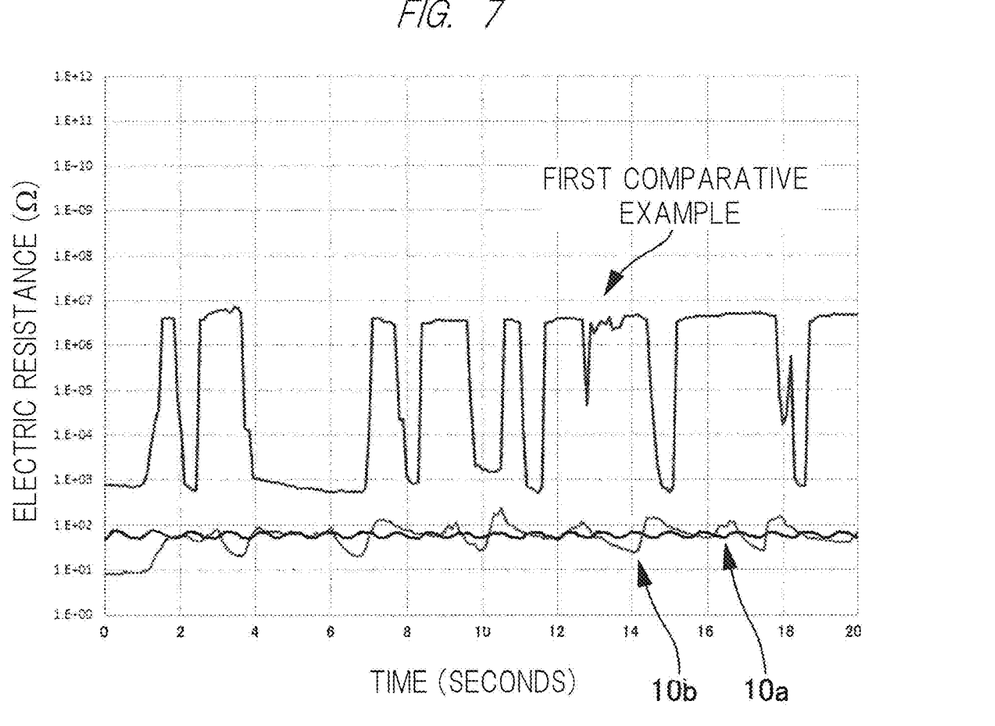
FIG. 7 is a graph of electric resistance change indicating results of an evaluation test for stretch/shrinkage.

As shown in FIG. 7, a stretch/shrinkage operation that stretches each of the raised electrodes 10a and 10b and the Ag paste electrode of the first comparative example by a factor of 1.5 in the direction along the main surface and that returns to the original state was repeated, and the electric resistance of the electrode region in the direction along the main surface was measured. In the first comparative example, the electric resistance was largely inconsecutively changed by the stretch/shrinkage operation. It is found that the electric resistance is large when the Ag paste electrode is stretched. On the other hand, in both the raised electrodes 10a and 10b, it is found that the degree of the change of the electric resistance in the stretch/shrinkage operation is small and is the consecutive change so as to maintain the good electric conductivity against the stretch. More specifically, the degree of the change of the electric resistance is smaller in the raised electrode 10a having the small angle of the conductive fiber 3 from the main surface of the base member 1 than the raised electrode 10b having the large angle thereof. As described above, it is found that the electric conductivity is easier to be maintained against the stretch in the direction along the main surface of the base member 1 as the angle of the conductive fiber 3 is smaller.

Figure 8:
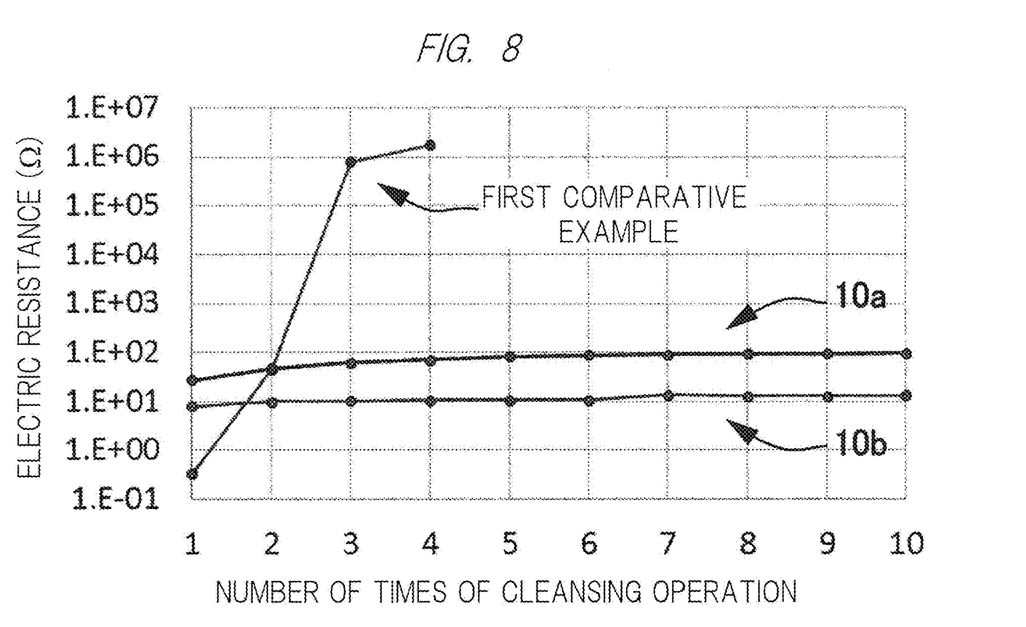
FIG. 8 is a graph of electric resistance indicating results of an evaluation test for cleansing endurance.

As shown in FIG. 8, the cleansing operation was repeated for each of the raised electrodes 10a and 10b and the Ag paste electrode of the first comparative example, and the electric resistance of the electrode region in the direction along the main surface of the base member 1 on the basis of the number of times of the execution of the cleansing operation was measured. In the Ag paste electrode of the first comparative example, the electric resistance adversely significantly increased by performing the cleansing operation only three times. It is thought that the Ag paste was separated in the direction along the main surface by the shape change caused by the electrode bending or others in the cleansing operation, and besides, the Ag paste was partially fallen down by water flow. On the other hand, in both the raised electrodes 10a and 10b, the large change of the electric resistance due to the cleansing operation was not observed at least until the cleansing operation was performed ten times. It is thought that the following ability of the resin layer 2 for the deformation caused by the bending or others is high, which results in suppression of the falling down of the conductive fibers 3 due to the cleansing operation.

As described above, it is found that each of the raised electrodes 10a and 10b follows the deformation, that is caused by the pressing and the stretch, better than the Ag paste electrode, can maintain the electric conductivity, and is excellent as the biological electrode.

FIRST PRACTICAL EXAMPLE

Figure 9:
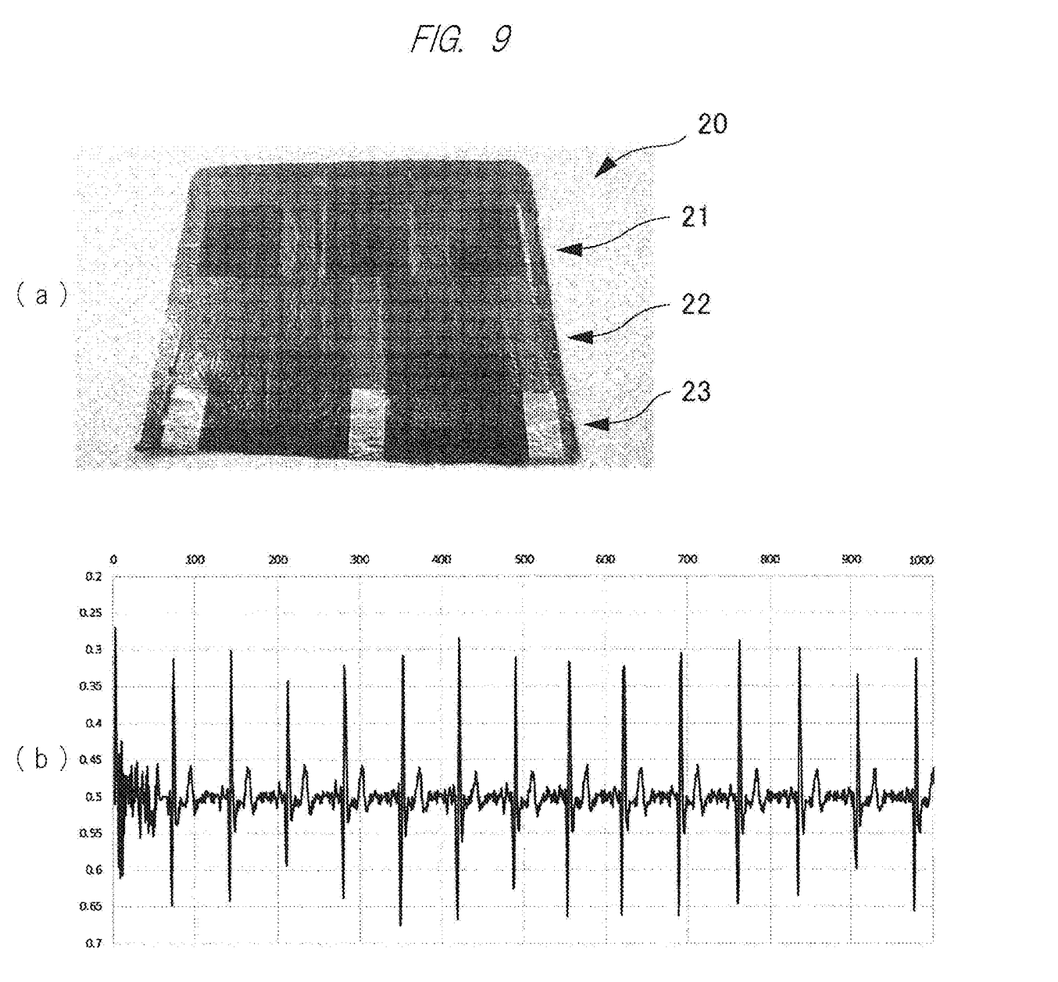
FIG. 9 is an exterior picture of and an obtained electrocardiographic waveform of a raised electrode in a first example.

As shown in FIG. 9(a), by the above-described manufacturing method, a raised electrode 20 was manufactured. In the raised electrode 20, three square electrode regions 21 made of the conductive fibers 3 were formed as shown on an upper side of a sheet of the drawing, and wiring regions 22 made of the conductive fibers 3 that extend downward from the respective electrode regions 21 were formed. As described above, each of the wiring regions 22 is a region where an insulating film made of an insulator is formed over a region in which the conductive fibers 3 are implanted. A terminal 23 was connected to a lower end of the wiring region 22.

As shown in FIG. 9(b), in the electrocardiogram-waveform measuring using the raised electrode 20, a clear waveform was able to be obtained, and it was verified that the raised electrode 20 can function well as the biological electrode for obtaining the electrocardiogram.

SECOND PRACTICAL EXAMPLE

Figure 10:
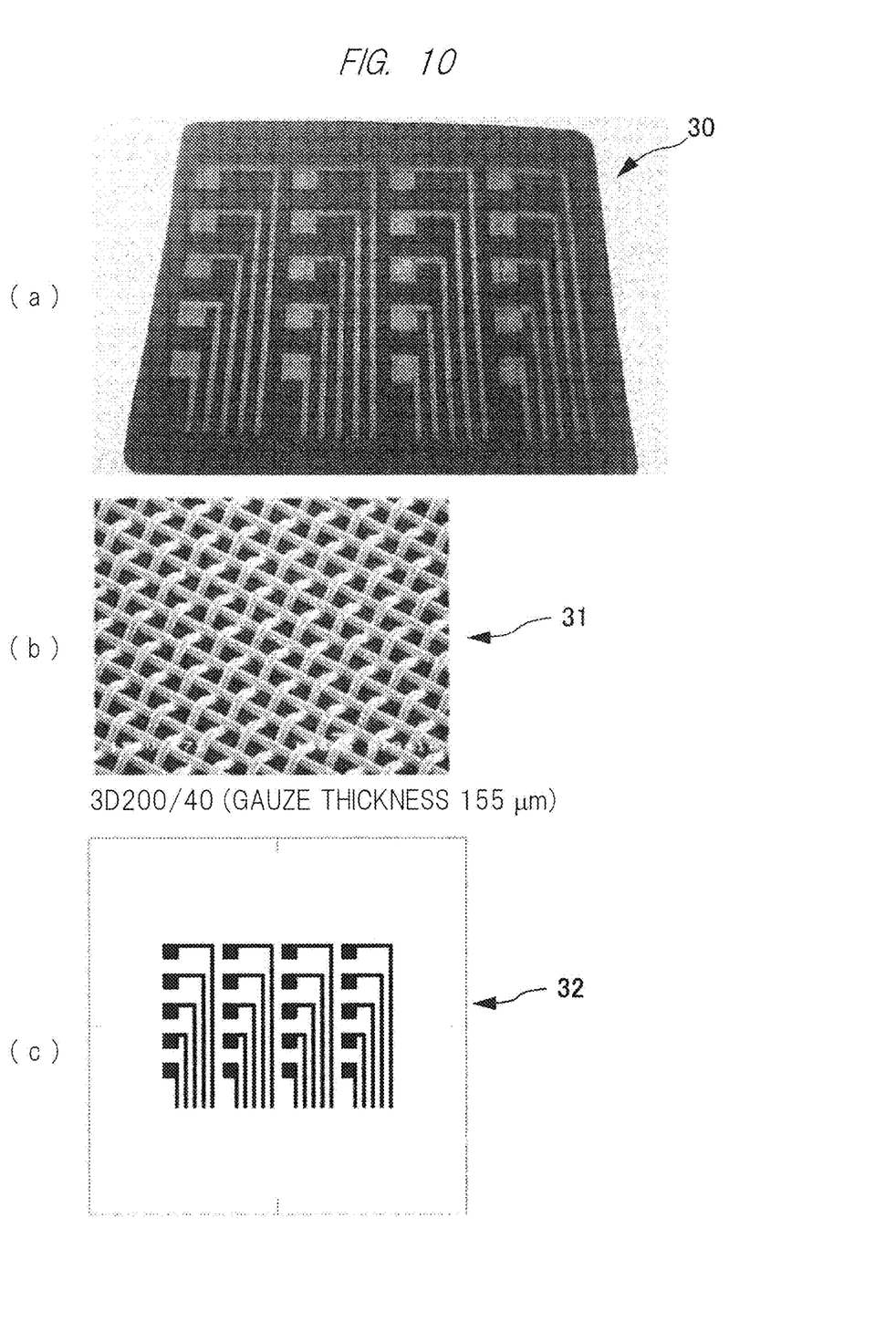
FIG. 10 is an exterior of a raised electrode in a second example, an enlarged view of mesh used for screen printing, and a pattern diagram of a screen mask.

A raised electrode 30 shown in FIG. 10(a) was manufactured by using a screen printing method and an electrostatic flocking method. The adhesive 2a was applied onto the base member 1 by the screen printing method (see FIG. 2), and the conductive fibers 3 were implanted by the electrostatic flocking method. As the adhesive 2a, acrylic emulsion produced by DIC corporation (product name: VONCOAT, W-386) was used.

With reference to FIG. 10(b), a mesh 31 used in the screen printing method is a 3D mesh with 200 mesh counts made of fibers each of which has a fiber diameter of 40 μm and each of which is thick to have a gauze thickness of 155 μm in order to allow the thick adhesive 2a to be applied. A screen plate was obtained by applying and drying photosensitive emulsion having a thickness of 50 μm on the mesh 31, pasting a posi-type film based on a screen mask that is produced by Mitani Micronics Co., Ltd., shown in FIG. 10(c), and performing exposure to light. Note that liquid-repellent coating was made on the screen plate so as not to cause plate piling of the adhesive 2a.

As described above, a raised electrode 30 having the formation mode of the conductive fibers 3 as described above was obtained even when the adhesive 2a was applied by the screen printing method so as to form the electrode pattern forming the electrode region (and the wiring region), and besides, even when the conductive fibers 3 were implanted by the electrostatic flocking method.

In the foregoing, the practical examples according to the present invention and the modification examples based on the practical examples have been described. However, the present invention is not always limited to the foregoing examples, and those who are skilled in the art could have conceived various alternative examples and modification examples within the scope of the concept of the present invention or the attached claims.

While the present disclosure has been illustrated and described with respect to a particular embodiment thereof, it should be appreciated by those of ordinary skill in the art that various modifications to this disclosure may be made without departing from the spirit and scope of the present disclosure.

The invention claimed is:

1. A raised electrode formed by raising a surface of a sheet material having a stretch property, comprising:
   a resin layer configured to be stretchable to follow the surface of the sheet material; and
   a plurality of conductive fibers each having an inserted portion, one end of which is inserted into the resin layer,
   wherein the plurality of conductive fibers that are adjacent to one another are electrically in contact with one another at non-inserted portions into the resin layer, and
   the plurality of conductive fibers are formed in the resin layer so as to have such a density as causing an in-plane isotropic electric conductivity of an electrode region of the sheet material in which the plurality of conductive fibers are formed,
   wherein the plurality of conductive fibers are inserted into the resin layer at an angle inclined with respect to a surface of the resin layer, which angle is not orthogonal or substantially orthogonal to the surface of the resin layer.

2. The raised electrode according to claim 1,
   wherein the plurality of conductive fibers that are adjacent to one another and have a contact point among them incline from the sheet material so as to maintain the contact point in stretch of the sheet material.

3. The raised electrode according to claim 2,
   wherein, in the plurality of conductive fibers, lengths of the inserted portions are smaller than lengths of the non-inserted portions.

4. The raised electrode according to claim 3,
   wherein each of the plurality of conductive fibers is a needle-shaped body having an electric-conductive plated surface of the fiber.

5. The raised electrode according to claim 1,
   wherein the lengths of the non-inserted portions of the plurality of conductive fibers is twice or more as long as the lengths of the inserted portions thereof.

6. The raised electrode according to claim 1,
   wherein a length of each of the plurality of conductive fibers is 1 mm or shorter.

7. The raised electrode according to claim 1, wherein the resin layer is an insulator.

8. A method of manufacturing a raised electrode formed by raising a surface of a sheet material having a stretch property, the raised electrode including: a resin layer configured to be stretchable to follow the surface of the sheet material; and a plurality of conductive fibers each having an inserted portion, one end of which is inserted into the resin layer, the method comprising:
- a step of forming an adhesive layer on the surface of the sheet material;
- a raising step of raising the surface by making the plurality of conductive fibers fly toward the surface, and inserting the one ends into the adhesive layer; and
- a hardening step of forming the resin layer by hardening the adhesive layer, wherein the plurality of conductive fibers that are adjacent to one another are electrically in contact with one another at non-inserted portions into the resin layer, and the plurality of conductive fibers are formed so as to have such a density as causing an in-plane isotropic electric conductivity of an electrode region of the sheet material in which the plurality of conductive fibers are formed, wherein the plurality of conductive fibers are inserted into the resin layer at an angle inclined with respect to a surface of the resin layer, which angle is not orthogonal or substantially orthogonal to the surface of the resin layer.

9. The method of manufacturing the raised electrode according to claim 8, wherein the raising step includes a spraying step of spraying the plurality of conductive fibers, in a charged state, from an electrostatic spray gun toward the sheet material in a state in which a voltage is applied between the electrostatic spray gun and an earthed electrode on which the sheet material is placed.

10. The method of manufacturing the raised electrode according to claim 9, wherein, in the spraying step, the voltage is adjusted so that lengths of the inserted portions of the plurality of conductive fibers are smaller than lengths of the non-inserted portions thereof.

11. The method of manufacturing the raised electrode according to claim 10, wherein, in the spraying step, the lengths of the non-inserted portions of the plurality of conductive fibers is twice or more as long as the lengths of the inserted portions thereof.

12. A raised electrode formed by raising a surface of a sheet material having a stretch property, comprising:
- a resin layer configured to be stretchable to follow the surface of the sheet material; and
- a plurality of conductive fibers each having an inserted portion, one end of which is inserted into the resin layer, wherein the plurality of conductive fibers that are adjacent to one another are electrically in contact with one another at non-inserted portions into the resin layer, and the plurality of conductive fibers are formed in the resin layer so as to have such a density as causing an in-plane isotropic electric conductivity of an electrode region of the sheet material in which the plurality of conductive fibers are formed, wherein, in the plurality of conductive fibers, lengths of the inserted portions are smaller than lengths of the non-inserted portions, wherein the plurality of conductive fibers are inserted into the resin layer at an angle inclined with respect to a surface of the resin layer, which angle is not orthogonal or substantially orthogonal to the surface of the resin layer.

* * * * *